United States Patent
Sakai et al.

(10) Patent No.: US 7,544,648 B2
(45) Date of Patent: Jun. 9, 2009

(54) HAIR SHAMPOO COMPOSITION

(75) Inventors: Hirokazu Sakai, Tokyo (JP); Yoshimasa Okamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 301 days.

(21) Appl. No.: 10/825,315

(22) Filed: Apr. 16, 2004

(65) Prior Publication Data
US 2004/0235689 A1 Nov. 25, 2004

(30) Foreign Application Priority Data
Apr. 17, 2003 (JP) .............................. 2003-112271

(51) Int. Cl.
C11D 1/14 (2006.01)
C11D 1/29 (2006.01)
C11D 3/32 (2006.01)
C11D 3/37 (2006.01)

(52) U.S. Cl. .................. 510/126; 510/127; 510/137; 510/159; 510/473; 510/501; 510/504; 424/70.24

(58) Field of Classification Search ................ 510/126, 510/127, 137, 159, 473, 501, 504; 424/70.24
See application file for complete search history.

(56) References Cited

U.S. PATENT DOCUMENTS

| | | | |
|---|---|---|---|
| 5,137,715 A * | 8/1992 | Hoshowski et al. | 424/70.17 |
| 5,656,668 A | 8/1997 | Motion et al. | |
| 6,060,612 A | 5/2000 | Hong et al. | |
| 6,379,659 B1 | 4/2002 | Ishida et al. | |
| 2004/0156815 A1* | 8/2004 | Sakai et al. | 424/70.21 |
| 2006/0036046 A1* | 2/2006 | Sakai et al. | 525/474 |

FOREIGN PATENT DOCUMENTS

| | | |
|---|---|---|
| EP | 0 190 010 | 8/1986 |
| EP | 0 739 625 | 10/1996 |
| EP | 1 166 766 | 1/2002 |
| JP | A-64-9913 | 1/1989 |
| JP | A-8-502058 | 3/1996 |
| JP | A-10-226674 | 8/1998 |
| JP | A-11-209248 | 8/1999 |
| JP | A-11-222416 | 8/1999 |
| JP | A-2001-316352 | 11/2001 |
| JP | A-2003-012474 | 1/2003 |
| JP | A-2003-500337 | 1/2003 |
| WO | WO 97/35548 | 10/1997 |
| WO | WO 00/44345 | 8/2000 |

* cited by examiner

*Primary Examiner*—Gregory R Del Cotto
(74) *Attorney, Agent, or Firm*—Oblon, Spivak, McClelland, Maier & Neustadt, P.C.

(57) ABSTRACT

The present invention relates to a hair shampoo composition containing (A) an amphipathic amide lipid, and (B), from 5 to 30 wt. % of sulfate surfactants which are each represented by the formula: $R-O-(C_2H_4O)_a-SO_3M$ (wherein, R represents a $C_{8-18}$ alkyl or alkenyl group, a stands for 0 or a positive integer, and M represents an alkali metal, alkaline earth metal, or the like); are made of from 30 to 45 wt. % of a sulfate exhibiting a=0, from 18 to 27 wt. % of another sulfate exhibiting a=1, from 10 to 20 wt. % of a further sulfate exhibiting a=2, and the balance of further sulfates exhibiting a=3 or greater; and contain the sulfates exhibiting a=0 to 2 in an amount of 70 wt. % or greater based on the total sulfates. The hair shampoo composition of the present invention is able to for example have good foaming property, provide foam with good lubrication upon shampooing, have smooth feel upon rinsing, impart a pleasant feel such as gloss, manageability, resilience and strength to the hair after shampooing, and protect the hair from physical or chemical stimulation to make it resistant to damage.

3 Claims, No Drawings

HAIR SHAMPOO COMPOSITION

FIELD OF THE INVENTION

The present invention relates to hair shampoo compositions which have, for example, good foaming performance, impart a pleasant feel to hair and prevent hair damage.

BACKGROUND OF THE INVENTION

Alkyl sulfates typified by sodium dodecyl sulfate have frequently been used as a cleansing component of an aqueous cleanser, because of their high detergency and ability to foam large amounts. They however do not produce satisfactory feeling upon cleansing owing to lack of lubrication between hair strands. In order to overcome this, polyoxyethylene-added alkyl sulfates (alkyl ether sulfates) have come to be used popularly in view of their pleasant feeling upon cleansing. Of the alkyl ether sulfates, those with an average of 2 moles of EO have been used most typically. They are composed of about 20 wt. % of alkyl ether sulfates with 0 mole of EO, 10 wt. % or greater of those with from 1 to 3 moles of EO, and the balance of those with 4 or greater moles of EO. Alkyl ether sulfates are however much inferior in foaming speed compared with alkyl sulfates. Mixed use of an alkyl sulfate and an alkyl ether sulfate improves lathering properties a little, but cannot attain both speedy foaming and pleasant feeling of the foam.

As a technique of improving the performance of a hair shampoo composition by adjusting the composition ratio of EO-added alkyl ether sulfates which differ depending on the molar number of ethylene oxide, disclosed is an aqueous shampoo composition, which contains from 5 to 50 wt. % of a surfactant component including alkyl ether sulfates with 1 to 8 moles of ethylene oxide and an amphoteric surfactant, and less than 5 wt. % of alkyl ether sulfates with 1 mole or less of ethylene oxide (International Patent Publication No. Hei 11-507079). This shampoo composition is utterly insufficient from the viewpoint of lathering properties.

Since hair is frequently exposed to physical stimulation by daily hair care routines such as heat drying with a hair dryer and brushing, and chemical stimulation by shampooing, permanent waving, dyeing and bleaching, it is often in a damaged state with a partial component or structural loss. An oil component such as silicone oil is added to impart a shampoo composition with protecting and restoring functions. An excess amount of such an oil component, however, causes problems such as deterioration in essential performances including lathering properties and ease of finger combing through the hair upon rinsing.

SUMMARY OF THE INVENTION

In the present invention, there is thus provided a hair shampoo composition containing the following components (A) and (B):

(A): an amphipathic amide lipid, and
(B): from 5 to 30 wt. % of sulfate surfactants which are each represented by the following formula (b):

$$R\text{—}O\text{—}(C_2H_4O)_a\text{—}SO_3M \quad (b)$$

(wherein, R represents a linear or branched alkyl or alkenyl group having from 8 to 18 carbon atoms, a stands for 0 or a positive integer, and M represents an alkali metal, alkaline earth metal, ammonium, alkanolamine or basic amino group); are made of from 30 to 45 wt. % of the sulfate exhibiting a=0, from 17 to 27 wt. % of the sulfate exhibiting a=1, from 10 to 20 wt. % of the sulfate exhibiting a=2, and the balance of the sulfates exhibiting a=3 or greater; and contain the sulfates exhibiting a=0 to 2 in an amount of 70 wt. % or greater based on the total sulfates.

DETAILED DESCRIPTION OF THE INVENTION

The present invention relates to a hair shampoo composition which has for example good foaming properties and provides foams with good lubrication upon shampooing, has smooth feel and imparts gloss, manageability and a pleasant feel such as resilience and strength to the hair upon rinsing, and protects the hair from physical or chemical stimulation to make it resistant to damage.

The amphipathic amide lipid as Component (A) preferably has 1 or 2 amide groups; preferably has, as a carbon chain bonded to the carbonyl group of the amide group, a $C_{5\text{-}60}$ alkyl or alkylene group which may be substituted with a hydroxy group and may contain an ester bond in its main chain; and preferably contains 1 to 5 hydroxy or $C_{1\text{-}30}$ alkoxy groups in total. The following compounds (A-1) to (A-4) are specific examples of the amphipathic amide lipid.

(A-1) Diamide compounds represented by formula (1):

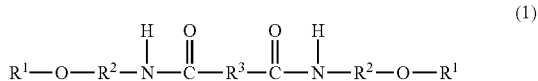

(1)

wherein, $R^1$ represents a linear or branched $C_{1\text{-}12}$ hydrocarbon group which may be substituted with a hydroxy group(s) and/or alkoxy group(s), $R^2$ represents a linear or branched divalent $C_{1\text{-}5}$ hydrocarbon group and $R^3$ represents a linear or branched divalent $C_{1\text{-}22}$ hydrocarbon group.

As $R^1$ in formula (1), linear or branched $C_{1\text{-}12}$ alkyl groups which may be substituted with 1 to 3 groups selected from a hydroxy group and $C_{1\text{-}6}$ alkoxy groups are preferred. Of these, unsubstituted $C_{1\text{-}12}$ alkyl groups and $C_{2\text{-}12}$ alkyl groups substituted with 1 to 2 hydroxy groups and one $C_{1\text{-}6}$ alkoxy group or with one hydroxy group and one $C_{1\text{-}6}$ alkoxy group are more preferred. Specific examples include methyl, ethyl, propyl, butyl, hexyl, dodecyl, 2-methylpropyl, 2-ethylhexyl, 2-hydroxyethyl, 9-hydroxynonyl, 2,3-dihydroxypropyl, 2-methoxyethyl, 2-hydroxy-3-methoxypropyl and 9-methoxynonyl groups, of which 2-hydroxyethyl, methyl, dodecyl and 2-methoxyethyl groups are preferred.

As $R^2$ in formula (1), linear or branched $C_{2\text{-}5}$ alkylene groups are preferred, and linear or branched $C_{2\text{-}3}$ alkylene groups are preferred. Specific examples include ethylene, trimethylene, tetramethylene, pentamethylene, 1-methylethylene, 2-methylethylene, 1-methyltrimethylene, 2-methyltrimethylene, 1,1-dimethylethylene and 2-ethyltrimethylene groups. Of these, ethylene and trimethylene groups are preferred.

As $R^3$ in formula (1), linear or branched divalent $C_{2\text{-}22}$ hydrocarbon groups are preferred, and linear or branched $C_{11\text{-}22}$ alkylene groups and alkenylene groups having 1 to 4 double bonds are more preferred. Specific examples include ethylene, trimethylene, tetramethylene, hexamethylene, heptamethylene, octamethylene, decamethylene, undecamethylene, dodecamethylene, tridecamethylene, tetradecamethylene, hexadecamethylene, octadecamethylene, 1-methylethylene, 2-ethyltrimethylene, 1-methylheptamethylene, 2-methylheptamethylene, 1-butylhexamethylene, 2-methyl-5-ethylheptamethylene, 2,3,6-trimethylheptamethylene, 6-ethyldecamethylene, 7-methyltetradecamethylene, 7-ethylhexadecamethylene, 7,12-dimethyloctadecamethylene, 8,11-dimethyloctadecamethylene, 7,10-dimethyl-7-ethylhexadecamethylene, 1-octadecylethylene, ethenylene, 1-octadecenylethylene, 7,11-octadecadienylene, 7-ethenyl-9-hexadecamethylene, 7,12-dimethyl-7,11-octadecadienylene and 8,11-dimethyl-7,11-octadecadienylene groups. Of these, 7,12-dimethyloctadecamethylene, 7,12-dimethyl-7,11-octadecadienylene, octadecamethylene, undecamethylene and tridecamethylene groups are preferred.

Preferred diamide compounds (1) are compounds having the above-described preferred groups as $R^1$, $R^2$ and $R^3$, respectively. Specific examples are the following compounds:

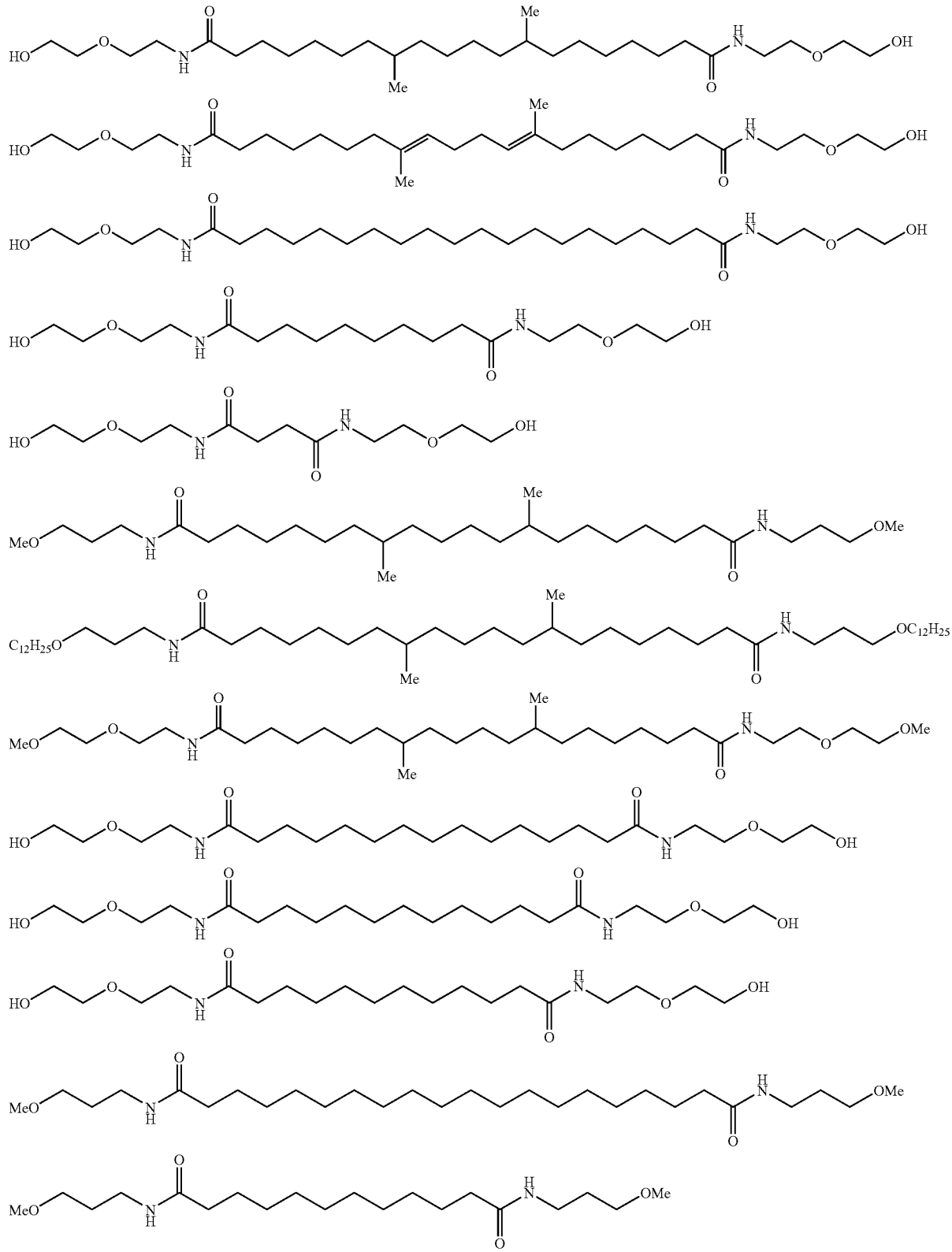

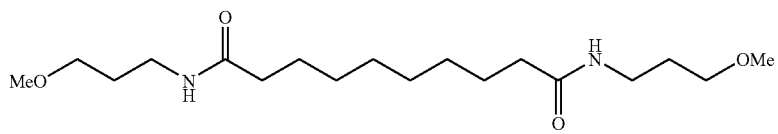

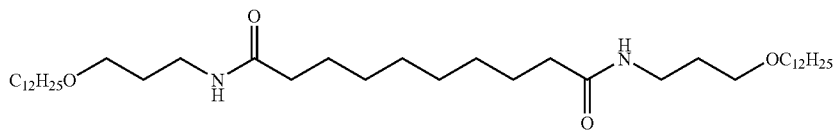

(A-2) Ceramides represented by the following formula (2):

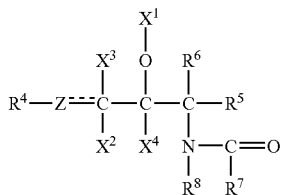
(2)

wherein, $R^4$ represents a linear, branched or cyclic, saturated or unsaturated $C_{4-30}$ hydrocarbon group which may be substituted with hydroxy, oxo or amino group(s), Z represents a methylene group, a methine group or an oxygen atom, a broken line represents the presence or absence of a π bond, $X^1$ represents a hydrogen atom, an acetyl group or a glyceryl group, or, together with the adjacent oxygen atom, forms an oxo group, $X^2$, $X^3$ and $X^4$ each independently represents a hydrogen atom, a hydroxy group or an acetoxy group (with the proviso that when Z represents a methine group, one of $X^2$ and $X^3$ represents a hydrogen atom and the other does not exist, and when —O—$X^1$ represents an oxo group, $X^4$ does not exist), $R^5$ and $R^6$ each independently represents a hydrogen atom, a hydroxy group, a hydroxymethyl group or an acetoxymethyl group, $R^7$ represents a linear, branched or cyclic, saturated $C_{5-35}$ hydrocarbon group which may be substituted with a hydroxy or amino group, or the saturated $C_{5-35}$ hydrocarbon group in which a linear, branched or cyclic, saturated or unsaturated $C_{8-22}$ fatty acid which may be substituted with hydroxy group(s) is ester-bonded at the ω-position of the hydrocarbon group, and $R^8$ represents a hydrogen atom or a linear or branched, saturated or unsaturated hydrocarbon group which may have substituent(s) selected from a hydroxy group, hydroxyalkoxy groups, alkoxy groups and an acetoxy group, and has 1 to 8 carbon atoms in total.

As $R^4$ in formula (2), linear, branched or cyclic, saturated or unsaturated $C_{7-22}$ hydrocarbon groups which may be substituted with hydroxy group(s) are preferred. As $X^1$, a hydrogen atom and a glyceryl group are preferred. It is preferred that none or one of $X^2$, $X^3$, and $X^4$ represents a hydroxy group and the others represent a hydrogen atom. It is preferred that one of $R^5$ and $R^6$ represents a hydrogen atom or a hydroxymethyl group and the other represents a hydrogen atom. In $R^7$, preferred examples of the fatty acid which may be ester-bonded or amide-bonded to the saturated hydrocarbon group at the ω-position thereof include isostearic acid, 12-hydroxystearic acid and linoleic acid. As $R^8$, a hydrogen atom and hydrocarbon groups which may be substituted with 1 to 3 substituents selected from a hydroxy group, hydroxyalkoxy groups and alkoxy groups and have 1 to 8 carbon atoms in total are preferred.

As ceramide (2), preferred are the following compounds (2a) and (2b).

(A-2a) Natural ceramides or natural type ceramides represented by formula (2a), and derivatives thereof (which will hereinafter be called "natural type ceramides")

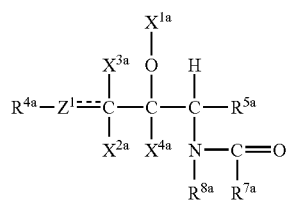
(2a)

wherein, $R^{4a}$ represents a linear, branched or cyclic, saturated or unsaturated $C_{7-19}$ hydrocarbon group which may be substituted with a hydroxy group, $Z^1$ represents a methylene or methine group, a broken line represents the presence or absence of a π bond, $X^{1a}$ represents a hydrogen atom or, together with the adjacent oxygen atom, forms an oxo group, $X^{2a}$, $X^{3a}$ and $X^{4a}$ each independently represents a hydrogen atom, a hydroxy group or an acetoxy group (with the proviso that when $Z^1$ represents a methine group, one of $X^{2a}$ and $X^{3a}$ represents a hydrogen atom and the other does not exist, and when —O—$X^{1a}$ represents an oxo group, $X^{4a}$ does not exist), $R^{5a}$ represents a hydroxymethyl group or an acetoxymethyl group, $R^{7a}$ represents a linear, branched or cyclic, saturated $C_{5-30}$ hydrocarbon group which may be substituted with hydroxy group(s), or the saturated $C_{5-30}$ hydrocarbon group in which a linear or branched, saturated or unsaturated $C_{8-22}$ fatty acid which may be substituted with hydroxy group(s) is ester-bonded at the ω-position of the hydrocarbon group, and $R^{8a}$ represents a hydrogen atom or a $C_{1-4}$ alkyl group.

Preferred are compounds in which $R^{4a}$ is a linear $C_{7-19}$, more preferably $C_{13-15}$ alkyl group, $Z^1$ is a methine group, one of $X^{2a}$ and $X^{3a}$ is a hydrogen atom, and $R^{7a}$ is a linear $C_{9-27}$ alkyl group which may be substituted with hydroxy group(s). In addition, $X^{1a}$ preferably represents a hydrogen atom or, together with an oxygen atom, forms an oxo group. Preferred examples of $R^{7a}$ include a tricosyl group, a 1-hydroxypentadecyl group, a 1-hydroxytricosyl group, a heptadecyl group, a 1-hydroxyundecyl group and a nonacosyl group having a linoleic acid ester-bonded at the ω-position of the group.

Specific examples of the natural type ceramides include Ceramide Types 1 to 7 having the below-described structures and obtained by amidation of sphingosine, dihydrosphingosine, phytosphingosine or sphingadienine (for example, FIG. 2 of J. Lipid Res., 24, 759(1983), and pig and human ceramides as described in FIG. 4 of J. Lipid Res., 35, 2069 (1994)).

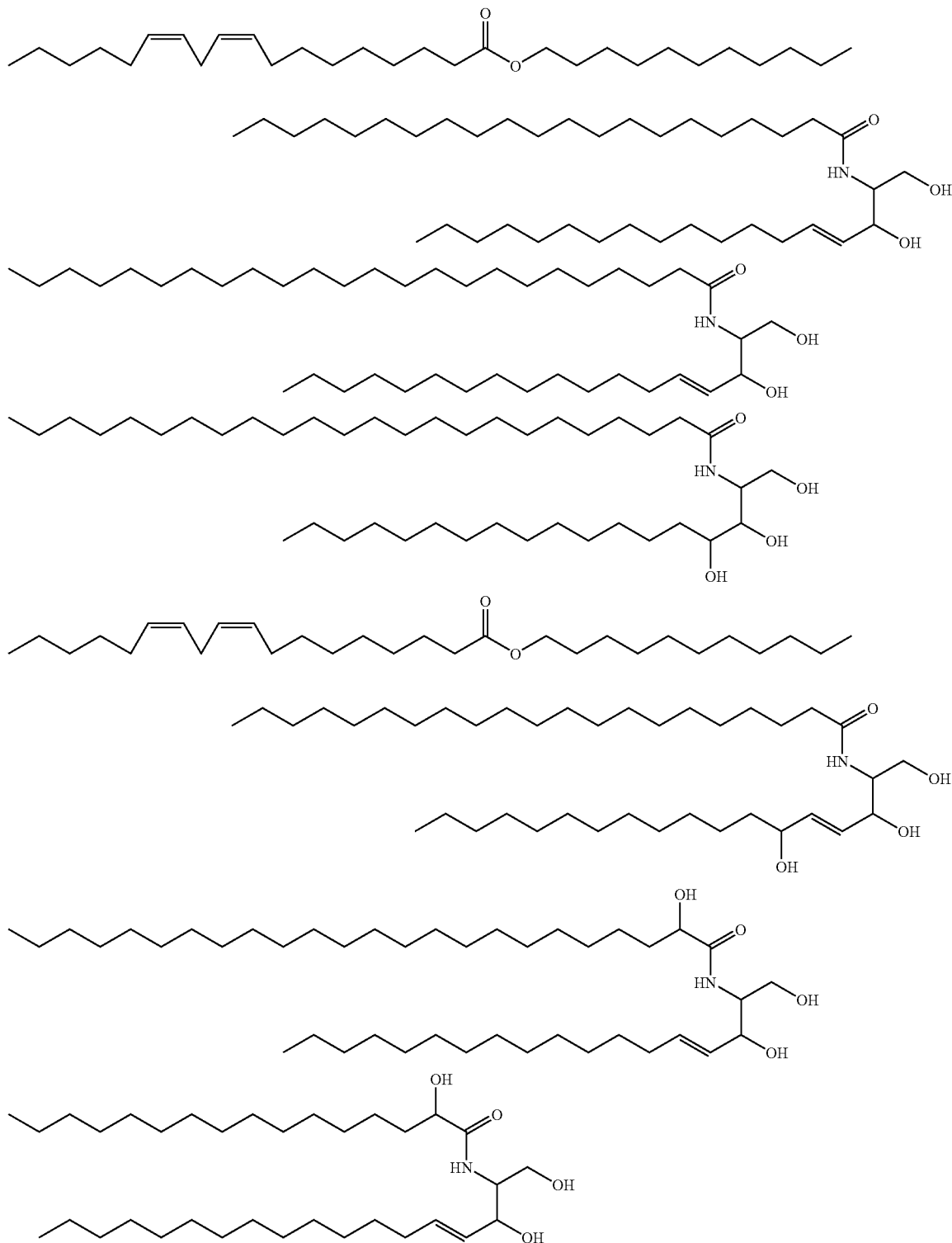

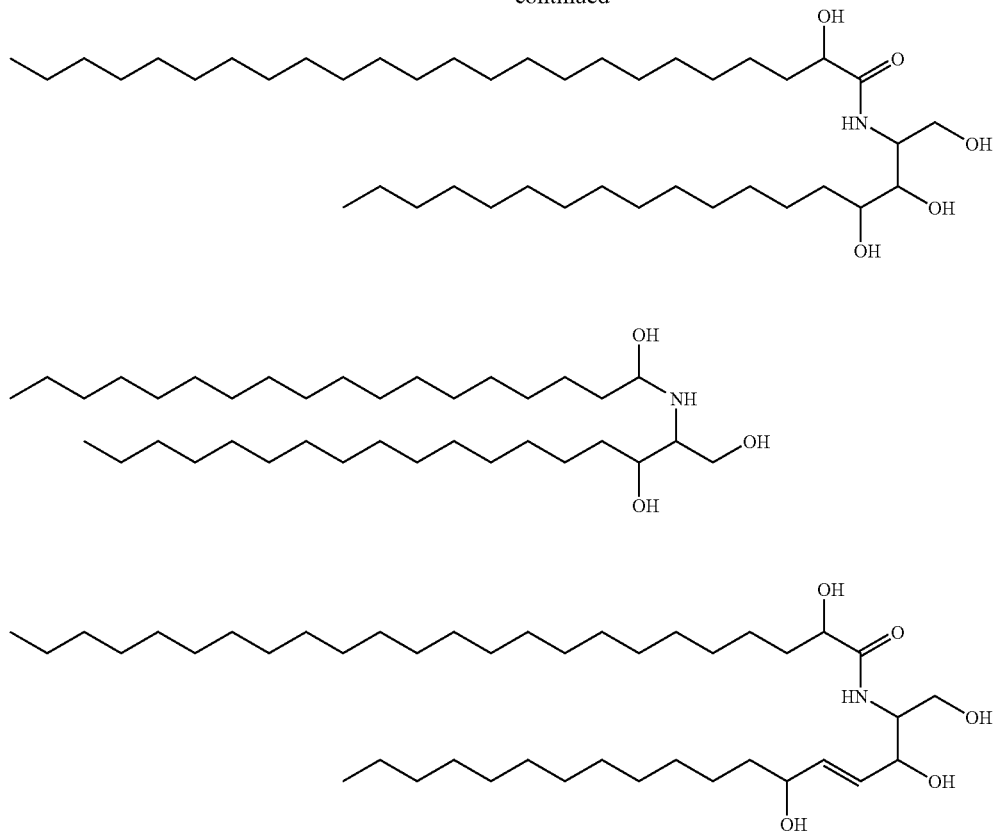

Examples also include N-alkyl derivatives (for example, N-methyl derivatives) of the above-described ceramides. They may be either a natural extract or synthesized product. Commercially available ones are also usable.

(A-2b) Pseudo type ceramides represented by the following formula (2b):

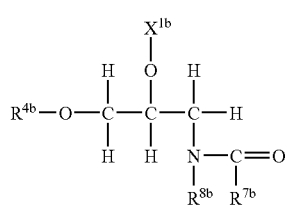

wherein, $R^{4b}$ represents a linear, branched or cyclic, saturated or unsaturated $C_{10-22}$ hydrocarbon group which may be substituted with hydroxy group(s), $X^{1b}$ represents a hydrogen atom, an acetyl group or a glyceryl group, $R^{7b}$ represents a linear, branched or cyclic, saturated or unsaturated $C_{5-22}$ hydrocarbon group which may be substituted with hydroxy or amino group(s), or the hydrocarbon group in which a linear or branched, saturated or unsaturated $C_{8-22}$ fatty acid which may be substituted with hydroxy group(s) is ester-bonded at the ω-position of the hydrocarbon group, and $R^{8b}$ represents a hydrogen atom or an alkyl group which may be substituted with hydroxy group(s), hydroxyalkoxy group(s), alkoxy group(s) or acetoxy group(s) and has 1 to 8 carbon atoms in total.

Preferred as $R^{7b}$ are a nonyl group, a tridecyl group, a pentadecyl group, an undecyl group having linoleic acid ester-bonded at the ω-position of the group, a pentadecyl group having linoleic acid ester-bonded at the ω-position of the group, a pentadecyl group having 12-hydroxystearic acid ester-bonded at the ω-position of the group, and an undecyl group having methyl-branched isostearic acid amide-bonded at the ω-position of the group. As the hydroxyalkoxy or alkoxy groups for $R^{8b}$, preferred are those having 1 to 8 carbon atoms.

As the pseudo type ceramides (2b), those having as $R^{4b}$ a hexadecyl group, as $X^{1b}$ a hydrogen atom, as $R^{7b}$ a pentadecyl group, and as $R^{8b}$ a hydroxyethyl group; those having as $R^{4b}$ a hexadecyl group, as $X^{1b}$ a hydrogen atom, as $R^{7b}$ a nonyl group, and as $R^{8b}$ a hydroxyethyl group; or those having as $R^{4b}$ a hexadecyl group, as $X^{1b}$ a glyceryl group, as $R^{7b}$ a tridecyl group, and as $R^{8b}$ a 3-methoxypropyl group are preferred, with those having as $R^{4b}$ a hexadecyl group, as $X^{1b}$ a hydrogen atom, as $R^{7b}$ a pentadecyl group, and as $R^{8b}$ a hydroxyethyl group being more preferred. Specific preferred examples include those represented by the following formulas:

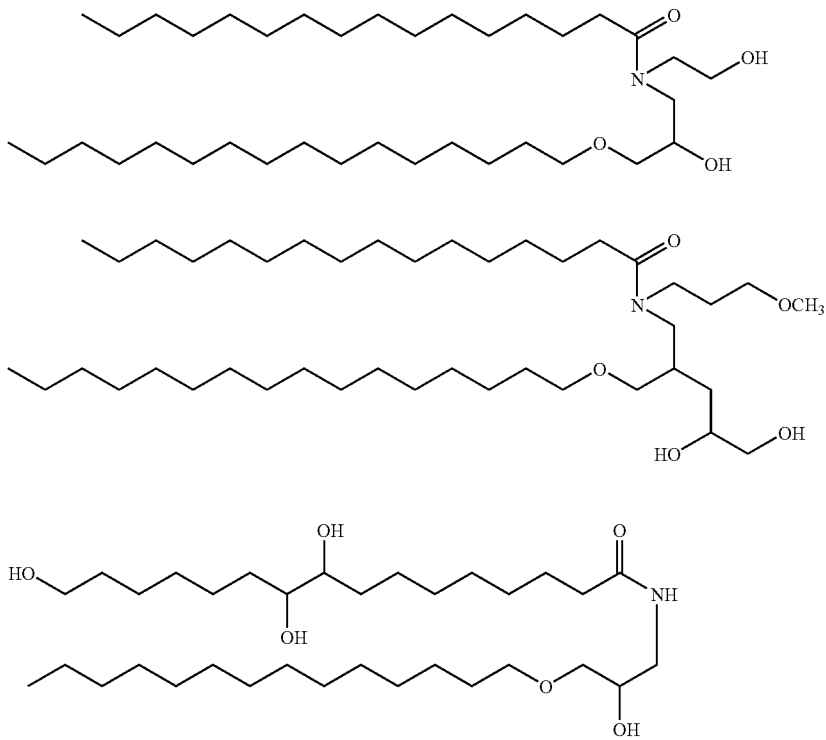

(A-3) Diamide compounds represented by the following formula (3):

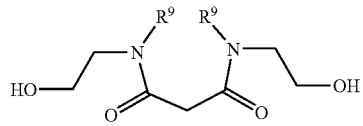

wherein, $R^9$ represents a $C_{10-18}$ alkyl group which may be substituted with hydroxy group(s).

Specific examples of compound (3) include the compound represented by the following formula:

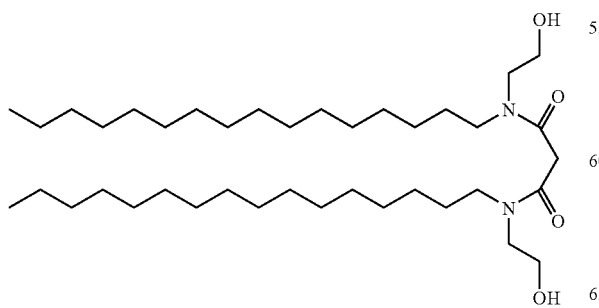

(A-4) Amide compounds represented by the following formula (4):

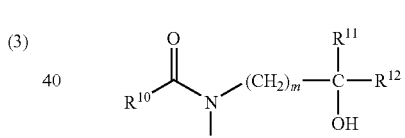

wherein, $R^{10}$ represents a linear or branched, saturated or unsaturated $C_{9-31}$ hydrocarbon group which may be substituted with hydroxy group(s), or a 2-dodecen-1-yl succinic acid residue, m stands for an integer of from 1 to 3, $R^{11}$ and $R^{12}$ each represents a hydrogen atom or a $C_{1-4}$ alkyl or hydroxyalkyl group, Y represents a linear or branched, saturated or unsaturated $C_{10-32}$ hydrocarbon group which may be substituted with hydroxy group(s), or a substituent represented by the following formula:

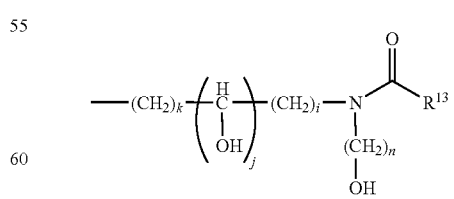

in which, k, i and n each stands for an integer of from 1 to 3, j stands for 0 or 1, and $R^{13}$ represents a linear or branched, saturated or unsaturated $C_{9-31}$ hydrocarbon group which may be substituted with hydroxy group(s).

Specific examples of Compound (4) include a compound represented by the following formula:

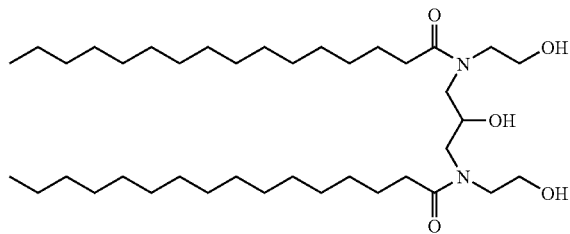

Of the above-described amphipathic amide lipids, those represented by formula (1) or (2b) are preferred, and those represented by formula (1) are more preferred.

As Component (A), two or more of these amphipathic amide lipids may be used in combination. Its (their) content in the hair cleansing composition of the present invention is preferably from 0.001 to 20 wt. %, more preferably from 0.1 to 20 wt. %, even more preferably from 0.5 to 15 wt. % in view of imparting firmness and body to hair and preventing split ends or breakage of hair.

In the present invention, as Component (B) serving as a surfactant, sulfates wherein the molar number of ethylene oxide added thereto fall within the above-described ranges are used from the viewpoint of attaining both speedy foaming and pleasant foam feel, of which those composed of from 33 to 43 wt. % of the sulfate exhibiting a=0, from 20 to 25 wt. % of the sulfate exhibiting a=1, from 13 to 18 wt. % of the sulfate exhibiting a=2 and the balance of the sulfates exhibiting a=3 or greater, each in all the sulfates, are preferred. In order to attain both speedy foaming and a pleasant foam feel, the sulfates exhibiting a=0 to 2 are preferably incorporated in this sulfate type surfactant in an amount of from 70 wt. % or greater, but more preferably 85 wt. % or greater of all the sulfates.

In formula (b), R represents a linear or branched alkyl or alkenyl group having from 8 to 18, more preferably from 10 to 16, still more preferably from 12 to 14 carbon atoms. M represents an alkali metal, an alkaline metal, ammonium, alkanolamine or basic amino group, with sodium, potassium, magnesium, and ammonium being preferred.

In the hair shampoo composition of the present invention, the content of the sulfate surfactant as Component (B) may range from 5 to 30 wt. %, preferably from 7 to 23 wt. %, more preferably from 10 to 20 wt. %.

The hair shampoo composition of the present invention may contain a nonionic surfactant or amphoteric surfactant as a surfactant other than the sulfate surfactant added as Component (B) in order to improve its cleansing performance.

Examples of the nonionic surfactant include polyoxyalkylene sorbitan fatty acid esters, polyoxyalkylene sorbitol fatty acid esters, polyoxyalkylene glycerin fatty acid esters, polyoxyalkylene fatty acid esters, polyoxyalkylene alkyl ethers, polyoxyalkylene alkylphenyl ethers, polyoxyalkylene (hydrogenated) castor oils, sucrose fatty acid esters, polyglycerin alkyl ethers, polyglycerin fatty acid esters, fatty acid alkanolamides, and alkyl glycosides. Of these, alkyl glycosides, polyoxyalkylene ($C_8$ to $C_{22}$) fatty acid esters, polyoxyethylene sorbitan fatty acid esters, polyoxyethylene hydrogenated castor oils and fatty acid alkanolamides are preferred. As the fatty acid alkanolamides, those with an acyl group having from 8 to 18, more preferably from 10 to 16 carbon atoms are preferred. As the fatty acid alkanolamides, either of monoalkanolamides or dialkanolamides may be used and those with a hydroxyalkyl group having 2 to 3 carbon atoms are preferred. Examples include oleic diethanolamide, palm kernel fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide and lauric acid monoethanolamide.

As the amphoteric surfactant, betaine surfactants may be used. Of these, betaine surfactants such as alkyldimethylaminoacetic acid betaines and fatty acid amidopropylbetaines are preferred, with fatty acid amidopropylbetaines being especially preferred. As the fatty acid amidopropylbetaines, those with an acyl group having from 8 to 18, more preferably from 10 to 16 carbon atoms are preferred, with lauryl amidopropylbetaine, palm kernel amidopropylbetaine and cocamidopropylbetaine being especially preferred.

The nonionic surfactant and amphoteric surfactant may be incorporated in the hair shampoo composition of the present invention as needed. Two or more of them may be used in combination. When the hair shampoo composition of the present invention is provided in the form of an aqueous liquid shampoo, use of fatty acid amidopropylbetaine or fatty acid alkanolamide is preferred, because it not only improves foaming power but also provides the shampoo with adequate fluidity.

The content of the nonionic surfactant in the hair shampoo composition may fall within a range of from 0 to 15 wt. %, more preferably from 0.5 to 10 wt. %, still more preferably from 1 to 5 wt. % in the hair shampoo composition, while that of the amphoteric surfactant in the hair shampoo composition may fall within a range of from 0 to 10 wt. %, more preferably 0.5 to 8 wt. %, still more preferably from 1 to 5 wt. %.

The hair shampoo composition of the present invention may further contain a cationic polymer in consideration of the texture of foams, lubricated feeling of foams, reduction in the friction between hair strands upon shampooing and smoothness after drying. Examples of the cationic polymer include cationic cellulose derivatives, cationic starch, cationic guar gum derivatives, homopolymers of a diallyl quaternary ammonium salt, diallyl quaternary ammonium salt/acrylamide copolymers, quaternized polyvinylpyrrolidone derivatives, polyglycol-polyamine condensation products, vinylimidazolium trichloride/vinylpyrrolidone copolymers, hydroxyethyl cellulose/dimethyldiallyl ammonium chloride copolymers, vinylpyrrolidone/quaternized dimethylaminoethyl methacrylate copolymers, polyvinylpyrrolidone/alkylamino acrylate copolymers, polyvinylpyrrolidone/alkylaminoacrylate/vinyl caprolactam copolymers, vinylpyrrolidone/methacrylamidopropyl trimethylammonium chloride copolymers, alkylacrylamide/acrylate/alkylaminoalkyl acrylamide/polyethylene glycol methacrylate copolymers, adipic acid/dimethylaminohydroxypropylethylenetriamine copolymers (CALTALETINE manufactured by US Sandos Corp.), and cationic polymers described in Japanese Patent Laid-Open No. Sho 53-139734 and Japanese Patent Laid-Open No. Sho 60-36407. Of these, cationic cellulose derivatives and cationic guar gum derivatives are preferred.

Two or more of these cationic polymers may be used in combination. Its content in the hair shampoo composition of the present invention is preferably from 0.02 to 5 wt. %, more preferably from 0.05 to 1 wt. %, and even more preferably from 0.1 to 0.3 wt. % from the viewpoints of improvement in the foam quality upon shampooing, manageability of hair after drying and improvement in feel.

The hair shampoo composition of the present invention may further contain a conditioning component such as silicone in order to improve the finish after drying. Examples of the silicone include dimethylpolysiloxane, methylphenylpolysiloxane, amino-modified silicone, polyether-modified silicone, epoxy-modified silicone, fluorine-modified silicone, cyclic silicones, alkyl-modified silicones, and oxazoline-modified silicone. Of these, dimethylpolysiloxane, methylphenylpolysiloxane, amino-modified silicone polyether-modified silicone, oxazoline-modified silicone and cyclic silicones are preferred. Two or more of these silicones may be used in combination. Its (their) content preferably ranges from 0.01 to 20 wt. %, more preferably from 0.05 to 10 wt. %, still more preferably from 0.1 to 5 wt. % in the hair shampoo composition of the present invention.

The hair shampoo composition of the present invention may contain, in addition to the above-described components, water soluble polymers such as hydroxypropylmethyl cellulose, hydroxyl cellulose, polyvinyl alcohol, and polyethylene glycol; polyhydric alcohols such as sorbitol; humectants; chelating agents such as ethylene diamine tetraacetic acid (EDTA); drugs such as vitamin preparations; amino acids and derivatives thereof; fine particles of a polymer such as polyethylene, polystyrene, poly(methyl methacrylate), nylon or silicone, and hydrophobic products thereof; extracts derived from animals or plants; ultraviolet absorbers; pearling agents, antiseptics; bactericides; pH regulators; colorants; and fragrances, according to the using purpose.

The hair shampoo composition of the present invention preferably has a pH of from 1 to 5, more preferably a pH of from 2 to 4.5, still more preferably a pH of from 3 to 4 when applied to hair (diluted to 20 times the weight with water, 25° C.) in view of improvement in the gloss or manageability of hair and penetration promotion of Component (A) to hair.

The hair shampoo composition of the present invention may be provided in any form selected from liquid, powder, gel and granule as needed. A liquid composition using water or a lower alcohol as a solvent is preferred, with a liquid composition using water being especially preferred.

Hair shampooed with the hair shampooing composition of the present invention acquires gloss and manageability, and pleasant feel such as resilience and strength, and at the same time, becomes resistant to damage, protected from physical or chemical stimulation. The hair shampoo composition of the present invention can be used in a conventional manner by applying it to hair, shampooing with it and then washing it away.

EXAMPLES

The present invention will hereinafter be described more specifically by Examples. It should however be borne in mind that the present invention is not limited to or by them.

In the below-described Examples and Comparative Examples, the pH is a value measured (by a pH meter) at 25° C. when a composition is diluted to 20 times the weight with water. The amphipathic amide lipid employed in the examples is either one of the following compounds.

Amphipathic Amide Lipid A

Amphipathic Amide Lipid B

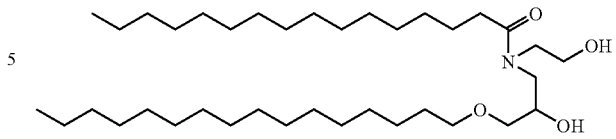

Preparation Example 1

In a closed pressure reactor were charged 2000 g of "KALCOL 2470" (trade name of dodecyl alcohol:tetradecyl alcohol=about 3:1, product of Kao Corporation) and 1.45 g of potassium hydroxide. After dehydration at 110° C. and 10 mmHg for 30 minutes, the reaction system was heated to 165° C. After heating, 456 g of ethylene oxide was pressed into the reaction mixture and addition reaction was effected for 30 minutes without changing the temperature. The reaction mixture was then cooled to 80° C., and neutralized with 1.3 g of acetic acid, whereby a mixture of the above-described raw material alcohol and ethylene oxide was obtained as an adduct.

Next, by using 1793 g of the mixture obtained above and 607 g of sulfur trioxide, sulfating reaction was performed at 40° C. The reaction mixture was then neutralized with 132 g of a 23 wt. % aqueous solution of sodium hydroxide and 556 g of deionized water. The concentration and pH of the reaction mixture were adjusted further with a 23 wt. % aqueous solution of sodium hydroxide, 75 wt. % of phosphoric acid and deionized water, whereby 10000 g of a 25 wt. % aqueous solution of Sulfate 1 as shown in Table 1 was obtained.

The sodium salt, sulfate salt, anion and EO chain of the sulfate thus obtained were confirmed in accordance with The Japanese Standards of Cosmetic Ingredients.

Examples 1 to 3 and Comparative Examples 1 to 3

With a sulfate surfactant (sodium lauryl ether sulfate) shown in Table 1, a hair shampoo composition as shown in Table 2 was prepared and its "foaming speed", "lubricated feeling upon shampooing", "gloss and manageability of hair after drying", and "resilience and strength of hair" were evaluated. The composition percentage in Table 1 was measured using gas chromatography.

(Foaming Speed)

Using the apparatus and conditions as described in columns [0053] and [0054] of Japanese Patent application Laid-Open No. Hei 10-73584, the amount of foam obtained by shampooing 0.3 mL of a model sebum with 1.5 mL of a sample to be evaluated was measured. The foaming speed was evaluated at the time the amount of foam reached 25 mL.

Evaluation Criteria
 A: less than 100 seconds
 B: 100 seconds or greater but less than 200 seconds
 C: 200 seconds or greater but less than 300 seconds
 D: 300 seconds or greater

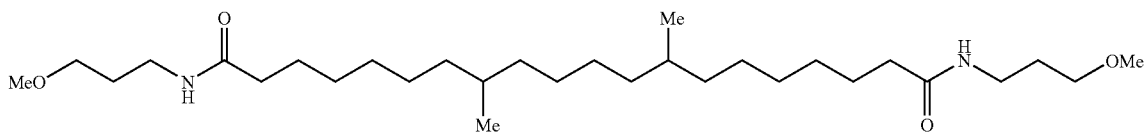

(Lubricated Feeling Upon Shampooing)

After a bundle of human hair 25 cm long, 5.5 cm wide and 10 g in weight was lightly rinsed with warm water of 40° C., excess water was removed. Foam was then made sufficiently for about 30 seconds with 0.5 g of a hair shampoo composition. The lubricated feeling of the hair bundle with foam was then organoleptically evaluated. It was indicated by the total scores of a panel of 5 experts.

Evaluation Criteria
  4: Good lubrication
  3: Slight lubrication
  2: Poor lubrication
  1: No lubrication (Gloss and Manageability After Drying)

After a hair bundle treated as in the evaluation of lubricated feeling was rinsed for 30 seconds with running water (2 L/min) of 40° C., it was towel dried sufficiently, followed by natural drying. After drying, the gloss and manageability were evaluated visually. It was indicated by the total scores of a panel of 5 experts.

Evaluation Criteria
  4: Good
  3: Fair
  2: Not so good
  1: Poor (Resilience and Strength of Hair After Drying)

Hair moisturized sufficiently was shampooed with 5 g or 10 g of a hair shampoo composition (5 g for semi-long hair and 10 g for long hair). After rinsing the hair well, it was dried enough with hot air from a dryer. Evaluation of the resilience and strength of hair was indicated by the total scores of a panel of 5 experts.
  4: A marked improvement in resilience and strength is observed.
  3. An improvement in resilience and strength is observed.
  2: A slight improvement in resilience and strength is observed.
  1: Neither resilience nor strength is improved.
  0: Resilience and strength are lost.

TABLE 1

Percentage (wt. %) of components of the sulfate surfactant by the molar number of EO

| | n in the formula (b) | | | | | | | | | | | | | |
|---|---|---|---|---|---|---|---|---|---|---|---|---|---|---|
| | 0 | 1 | 2 | 3 | 4 | 5 | 6 | 7 | 8 | 9 | 10 | 11 | 12 | 13 |
| Sulfate 1 | 40.64 | 22.29 | 14.80 | 8.68 | 4.90 | 2.99 | 1.91 | 1.32 | 0.92 | 0.62 | 0.42 | 0.27 | 0.17 | 0.08 |
| Sulfate 2 | 34.29 | 21.41 | 16.59 | 10.09 | 5.77 | 3.60 | 2.35 | 1.72 | 1.29 | 0.96 | 0.71 | 0.49 | 0.43 | 0.31 |
| Comparative sulfate 1 | 46.43 | 10.70 | 10.73 | 8.83 | 6.45 | 4.71 | 3.43 | 2.65 | 2.04 | 1.56 | 1.19 | 0.82 | 0.41 | 0.04 |
| Comparative sulfate 2 | 19.97 | 15.99 | 16.03 | 13.20 | 9.64 | 7.04 | 5.13 | 3.96 | 3.05 | 2.33 | 1.78 | 1.23 | 0.62 | 0.05 |

Sulfate 1: prepared in Preparation Example 1
Sulfate 2: prepared in accordance with Preparation Example 1
Comparative sulfate 1: a mixture of a lauryl ether sulfate having 2.0 moles, on average, of EO (comparative sulfate 2) and a lauryl sulfate
Comparative sulfate 2: a lauryl ether sulfate having 2.0 moles, on average, of EO ("Emal 227-PH11", product of Kao Corporation)

TABLE 2

(wt. %)

| | | Examples | | | Comparative Examples | | |
|---|---|---|---|---|---|---|---|
| | | 1 | 2 | 3 | 1 | 2 | 3 |
| (A) | Amphipathic amide lipid A | 2 | 2 | — | — | 2 | 2 |
| | Amphipathic amide lipid B | — | — | 2 | — | — | — |
| (B) | Sulfate 1 | 10 | — | 10 | 10 | — | — |
| | Sulfate 2 | — | 10 | — | — | — | — |
| | Comparative sulfate 1 | — | — | — | — | 10 | — |
| | Comparative sulfate 2 | — | — | — | — | — | 10 |
| Others | Dimethylpolysiloxane emulsion *1 | 2 | 2 | 2 | 2 | 2 | 2 |
| | Myristyl alcohol | 1 | 1 | 1 | 1 | 1 | 1 |
| | Cocoylmonoethanolamide | 0.5 | 0.5 | 0.5 | 0.5 | 0.5 | 0.5 |
| | Ethylene glycol distearyl ester | 1 | 1 | 1 | 1 | 1 | 1 |
| | Cationic hydroxyethylcellulose | 0.3 | 0.3 | 0.3 | 0.3 | 0.3 | 0.3 |
| | Cationic guar gum | 0.5 | 0.5 | 0.5 | 0.5 | 0.5 | 0.5 |
| | Malic acid | 1 | 1 | 1 | 1 | 1 | 1 |
| | 50 wt. % NaOH aq. soln/50 wt. % citric acid | q.s. *2 | q.s. *2 | q.s. *2 | q.s. *2 | q.s. *2 | q.s. *2 |
| | Purified water | Balance | Balance | Balance | Balance | Balance | Balance |
| pH | | 3.5 | 3.5 | 3.5 | 3.5 | 3.5 | 3.5 |
| Buffering capacity (NgOH-gram equivalent/L) | | 0.01 | 0.01 | 0.01 | 0.01 | 0.01 | 0.01 |
| Evaluation | Foaming speed | A | A | A | C | C | C |
| | Lubricated feeling of foam | 18 | 20 | 20 | 9 | 15 | 7 |
| | Gloss and manageability | 19 | 20 | 15 | 6 | 18 | 18 |
| | Resilience and strength of hair | 20 | 19 | 17 | 9 | 11 | 12 |

*1: "CF-2460" (trade name; product of Dow Corning Toray Silicone, a 75 wt. % emulsion, average particle size: about 100 μm)
*2: Amount enough for pH adjustment

Example 4

Pearlescent Shampoo

|  | (wt. %) |
| --- | --- |
| Sulfate 1 | 8.0 |
| Lauroylamidopropylbetaine | 3.0 |
| Cocoylmonoethanolamide | 0.7 |
| Ethylene glycol distearate | 3.0 |
| Cationic hydroxyethylcellulose | 0.2 |
| Amphipathic amide lipid A | 2.0 |
| Glycerin | 1.0 |
| Salicylic acid | Amount enough for pH adjustment |

Deionized Water Balance

The above-described shampoo (pH 3.7) foams speedily, can impart good smoothness and moist feeling to the hair after shampooing and inhibit the appearance of split ends or broken hair.

Example 5

Conditioning Shampoo

|  | (wt.%) |
| --- | --- |
| Sulfate 1 | 13.0 |
| Cocoyl monoethanolamide | 1.0 |
| Myristyl alcohol | 1.0 |
| Distearyl alcohol | 2.0 |
| Cationic hydroxyethylcellulose | 0.3 |
| Amphipathic amide lipid B | 2.0 |
| Glycerin | 1.0 |
| Sodium chloride | 0.2 |
| Lactic acid | 0.1 |
| Malic acid | Amount enough for pH adjustment |
| Deionized water | Balance |

The above-described shampoo (pH3.7) can impart good smoothness and moist feeling to the hair after shampooing and inhibit the appearance of split ends or broken hair.

Example 6

Conditioning Shampoo

|  | (wt. %) |
| --- | --- |
| Sulfate 1 | 13.0 |
| Cocoyl monoethanolamide | 1.0 |
| Myristyl alcohol | 1.0 |
| Cetanol | 0.5 |
| Distearyl alcohol | 2.0 |
| Cocoyl benzalkonium chloride | 0.1 |
| Amphipathic amide lipid B | 2.0 |
| Cationic guar gum | 0.3 |
| Glycerin | 1.0 |
| Dimethicone (viscosity: 100000 mPa · s) | 0.5 |
| Sodium chloride | 0.2 |
| Benzyl alcohol | 0.5 |
| Malic acid | Amount enough for pH adjustment |
| Deionized water | Balance |

The above-described shampoo (pH 3.7) foams speedily and foam made thereby have good lubrication. In addition, it can impart good smoothness and moist feeling to the hair after shampooing and inhibit the appearance of split ends or broken hair.

Example 7

Pearlescent Antidandruff Shampoo

|  | (wt.%) |
| --- | --- |
| Sulfate 1 | 13.0 |
| Cocoyl monoethanolamide | 6.0 |
| Myristyl alcohol | 2.0 |
| Cetanol | 0.5 |
| Cationic guar gum | 0.3 |
| Amphipathic amide lipid A | 2.0 |
| Malic acid | 1.0 |
| Sodium chloride | 0.2 |
| Benzyloxyethanol | 0.5 |
| Dimethicone (viscosity: 100000 mPa · s) | 0.5 |
| Amodimethicone (product of Dow Corning Toray Silicone "SM8704C") | 0.1 |
| Ethylene glycol distearate | 3.0 |
| Cocoyl benzalkonium chloride | 0.5 |
| Cationic hydroxyethylcellulose | 0.3 |
| Glycerin | 1.0 |
| Sodium hydroxide | Amount enough for pH adjustment |
| Deionized water | Balance |

The above-described shampoo (pH 3.7) can impart good smoothness and moist feeling to the hair after shampooing and inhibit the appearance of split ends or broken hair.

The invention claimed is:

1. A hair shampoo composition comprising the following components (A) to (C):

(A): 0.5 to 2 wt. % of an amphipathic amide lipid of the formula

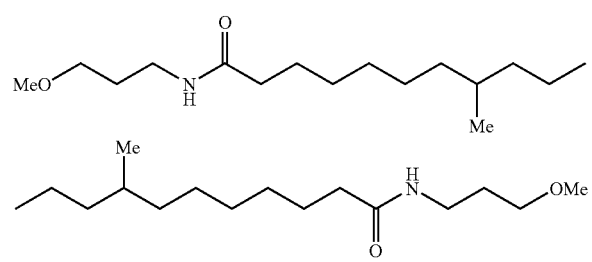

(B): from 7 to 10 wt. % of sulfate surfactants which are each represented by the following formula (b):

$$R\text{—}O\text{—}(C_2H_4O)_a\text{—}SO_3M \qquad (b)$$

wherein, R represents a linear or branched alkyl or alkenyl group having from 8 to 18 carbon atoms, a stands for 0 or a positive integer, and M represents an alkali metal, alkaline earth metal, ammonium, alkanolamine or basic amino group; are made of from 30 to 45 wt. % of the sulfate exhibiting a=0, from 17 to 27 wt. % of the sulfate exhibiting a=1, from 10 to 20 wt. % of the sulfate exhibiting a=2, and the balance of the sulfates exhibiting a=3 or greater; and contain the sulfates exhibiting a=0 to 2 in an amount of 70 wt. % or greater based on the total sulfates; and (C) 0.1 to 1 wt. % of a cationic polymer selected from the group consisting of cationic cellulose derivatives and cationic guar gum derivatives, and mixtures thereof, wherein said shampoo composition has a pH of from 3 to 4 at 25° C. when diluted to 20 times its weight with water.

2. The hair shampoo composition of claim 1, wherein component (B) is a sulfate type surfactant which is made of from 33 to 43 wt. % of the sulfate exhibiting a=0, from 20 to 25 wt. % of the sulfate exhibiting a=1, from 13 to 18 wt. % of the sulfate exhibiting a=2, and the balance of the sulfates exhibiting a=3 or greater; and the sulfates exhibiting a=0 to 2 are incorporated in an amount of from 85 wt. % or greater based on all the sulfates.

3. A hair protecting method, which comprises the steps of applying a hair shampoo composition as claimed in claim 1 to the hair, shampooing with the composition, and then rinsing off the composition.

* * * * *